(12) United States Patent
Koelker et al.

(10) Patent No.: US 10,330,627 B2
(45) Date of Patent: Jun. 25, 2019

(54) BIOSENSORS AND BIOSENSOR SYSTEMS WITH $MN_2O_3$ CATALYST AS WELL AS METHODS OF MAKING AND USING THE SAME

(71) Applicant: Roche Diabetes Care, Inc., Indianapolis, IN (US)

(72) Inventors: Karl-Heinz Koelker, Gruenstadt (DE); Arnulf Staib, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 446 days.

(21) Appl. No.: 14/199,003

(22) Filed: Mar. 6, 2014

(65) Prior Publication Data

US 2014/0251826 A1 Sep. 11, 2014

(30) Foreign Application Priority Data

Mar. 6, 2013 (EP) ..................................... 13157968

(51) Int. Cl.
*G01N 27/327* (2006.01)
*C12Q 1/00* (2006.01)
*A61B 5/1486* (2006.01)
*G01N 33/543* (2006.01)

(52) U.S. Cl.
CPC ....... *G01N 27/3271* (2013.01); *A61B 5/1486* (2013.01); *C12Q 1/004* (2013.01); *C12Q 1/006* (2013.01); *G01N 27/3272* (2013.01); *G01N 33/5438* (2013.01); *A61B 5/14865* (2013.01); *A61B 2562/0209* (2013.01); *A61B 2562/125* (2013.01); *A61B 2562/166* (2013.01)

(58) Field of Classification Search
CPC ....................... G01N 33/5438; G01N 27/3272
See application file for complete search history.

(56) References Cited

U.S. PATENT DOCUMENTS

| 4,679,562 | A | * | 7/1987 | Luksha | ................ | C12Q 1/006 |
| | | | | | | 204/415 |
| 5,225,064 | A | * | 7/1993 | Henkens | ............... | C12Q 1/003 |
| | | | | | | 204/403.1 |
| 6,706,473 | B1 | | 3/2004 | Edman et al. | | |
| 2006/0231417 | A1 | * | 10/2006 | Harding | ............. | G01N 27/3272 |
| | | | | | | 205/775 |

(Continued)

FOREIGN PATENT DOCUMENTS

| EP | 0603154 A2 | 6/1994 |
| JP | S56119837 A | 9/1981 |
| WO | 2012/130841 A1 | 10/2012 |

OTHER PUBLICATIONS

Dictionary.com, Definition of Particle. http://www.dictionary.com/browse/particle. No Date.*

(Continued)

*Primary Examiner* — Matthew D Krcha

(57) ABSTRACT

Biosensors and biosensor systems are disclosed that have manganese (III) oxide ($Mn_2O_3$)-based electrodes that can attenuate interference of a detection signal resulting from an analyte-relevant reaction caused by undesired reaction of interferents in a sample. Methods are also disclosed for making and using the same.

24 Claims, 6 Drawing Sheets

(56) References Cited

U.S. PATENT DOCUMENTS

| | | | |
|---|---|---|---|
| 2007/0007133 A1* | 1/2007 | Mang | A61B 5/14532 204/403.14 |
| 2007/0135698 A1* | 6/2007 | Shah | C12Q 1/006 600/348 |
| 2009/0071846 A1* | 3/2009 | Staib | C12Q 1/001 205/777.5 |
| 2012/0228138 A1 | 9/2012 | West et al. | |

OTHER PUBLICATIONS

Cui et al., "Amperometric biosensors based on carbon paste electrodes modified with nanostructured mixed-valence manganese oxides and glucose oxidase," Nanomedicine, 2005, pp. 130-135, 1. (Year: 2005).*

Turkusic et al., "Amperometric Determination of Glucose with an MnO2 and Glucose Oxidase Bulk-Modified Screen-Printed Carbon Ink Biosensor," Analytical Letters, 2001, pp. 2633-2647, 34(15). (Year: 2001).*

Nikan et al., "A new hydrogen peroxide biosensor by using modified Carbon Paste Electrode with catalase enzyme and Mn2O3 Nanoparticles," Annals of Biological Research, 2012 pp. 5242-5251, 3(11). (Year: 2012).*

Huang, Shan et al., "Glucose Biosensor Using Glucose Oxidase and Electrospun Mn2O3—Ag Nanofibers," Electroanalysis, 2011, pp. 1912-1920, vol. 23, No. 8.

Lin, Meng Shan and Leu, Joang Jyh, "A Fe3O4-Based Chemical Sensor for Cathodic Determination of Hydrogen Peroxide," Electroanalysis, 2005, pp. 2068-2073, vol. 17, No. 22.

Wang, Joseph, "Electrochemical Glucose Biosensors," Chemical Reviews, 2008, pp. 814-825, vol. 108.

Mohseni et al., Voltammetry behaviour of modified carbon paste electrode with cytochrome C and Mn2O3 nanoparticles for hydrogen peroxide sensing, International Journal of Electrochemical Science, 2012, pp. 12098-12109, 7.

Dodevska T. et al., Electrocatalytic reduction of hydrogen peroxide on modified graphite electrodes: application to the development of glucose biosensors, Analytical Bioanal. Chemistry, 2006, pp. 1413-1418, vol. 386.

* cited by examiner

BIOSENSORS AND BIOSENSOR SYSTEMS WITH $Mn_2O_3$ CATALYST AS WELL AS METHODS OF MAKING AND USING THE SAME

CROSS-REFERENCE TO RELATED APPLICATIONS

This patent application claims priority to and the benefit of EP Patent Application No. 13 157 968.2; filed 6 Mar. 2013, which is incorporated herein by reference as if set forth in its entirety.

TECHNICAL FIELD

This disclosure relates generally to chemistry and medicine, and more particularly, it relates to biosensors and biosensor systems having manganese (III) oxide ($Mn_2O_3$)-based electrodes that can attenuate interference of a detection signal resulting from an analyte-relevant reaction caused by undesired reaction of interferents in a sample, as well as methods of making and using the same.

BACKGROUND

Sensors, and particularly biosensors, are used in many technical fields to analyze a sample and to determine the concentration of an analyte present in the sample and/or to determine other parameters of the sample. Such sensors find use in, for example, water analysis (i.e., drinking water analysis), the food industry, the military and medicine among others.

Biosensors are known that use metal oxides as catalysts, where the catalysts accelerate the conversion reaction of hydrogen peroxide ($H_2O_2$), which is mediated by an analyte-specific enzyme. For example, EP Patent Application Publication No. 0 603 154 discloses that biosensor electrode material can include manganese (IV) oxide ($MnO_2$). Additional examples of catalysts disclosed include the following: $FeOOH$, $Fe_3O_4$, $Fe_2O_3$, $Cr_2O_3$ and $V_2O_5$. The biosensors are used with a voltage of between 350 mV to 500 mV. Unfortunately, the risk of these ranges for the working electrode voltage is an undesired reaction of further components (or interferents) in the sample, such as other metabolites or therapeutic agents. Metabolites that can be oxidized in the voltage range of 350 mV to 500 mV are, among others, uric acid and ascorbic acid. A typical example of a therapeutic agent that can be oxidized in this voltage range is acetaminophen. The oxidation of these interferents at the working electrode leads to an undefined increase of the electrode signal. At present, there is not an adequate means to distinguish the signal resulting from the analyte-relevant reaction of the $H_2O_2$ and the signal resulting from the undesired reaction of the interferents. Thus, the signal detected by the biosensor can be a mixture of both reactions. As these signals cannot be separated after detection, the analyte signal is overloaded by the interferent signal. Consequently, such measurements may lead to a false and imprecise detection of the analyte.

Catalysts, such as hexacyanoferrate catalysts, also are known that lead to a reduction of the analyte in a negative voltage range, which do not lead to reduced cross-reactions, as oxygen is reduced in the negative voltage range at about −0.1 V to −0.2 V.

Many currently used biosensors therefore show a high cross reactivity with a number of metabolites or other interferents that are present in a living body. As such, there is a need for biosensors applicable in biological systems, such as the living body, to detect analytes, such as glucose or other metabolites, in a precise and reproducible manner.

BRIEF SUMMARY

In view of the disadvantages noted above, the disclosure describes methods of detecting an analyte in a fluid sample even in the presence of certain interferents, thereby providing a more "true" analyte concentration. The methods are based upon an inventive concept that includes using manganese (III) oxide ($Mn_2O_3$)-based electrodes in biosensors and biosensor systems so that the detection reactions are less affected by certain interferents that may be present in the sample. In particular, it has been found that by using $Mn_2O_3$ particles in electrodes, the reduction reaction of $H_2O_2$ can be achieved in a voltage range where a reduction of oxygen ($O_2$) does not occur. Thus, the resulting analyte detection reaction is not falsified by a reaction of $O_2$ at any electrode. The inventive concept therefore provides certain advantages, effects, features and objects when compared to known methods of measuring an analyte concentration in a body fluid sample.

In one aspect, a method is provided for manufacturing a biosensor for detecting an analyte of interest in a sample. The method includes the step of providing a substrate having a sensor surface, where at least a part of the sensor surface is superimposed by a first conductive material. The method also includes the step of applying a first electrode material onto at least a part of the first conductive material to form a first electrode, where the first electrode material is adapted to perform at least one detection reaction when the analyte of interest is present in the sample. In some instances, the first electrode material includes $Mn_2O_3$ particles.

In another aspect, a method is provided for detecting an analyte of interest in a sample. The method includes the steps of providing a biosensor as described herein, applying to the biosensor a sample suspected of having the analyte of interest and applying a voltage to the working electrode of the biosensor, where the voltage is within a voltage range at which $H_2O_2$ in the sample is reduced at the working electrode.

The voltage range can be from about 50 mV to about 150 mV.

The method also can include the step of measuring an $H_2O_2$-dependent current and determining an analyte concentration therefrom.

In view of the methods above, a biosensor is provided for detecting an analyte of interest in a sample. The biosensor can include a substrate having a sensor surface, a conductive material superimposing at least a part of the sensor surface, and a first electrode material superimposing at least a part of the conductive material to form a working electrode, where the first electrode material can include $Mn_2O_3$ particles. The biosensor also can include at least one further electrode, such as a reference electrode, a counter electrode or even a combined reference/counter electrode.

Likewise, a biosensor system is provided for detecting an analyte of interest in a sample, where the system includes at least one biosensor as described herein. The biosensor system also includes at least one detector device, where the detector device is electrically connectable to the working electrode and to at least one further electrode of the biosensor. The detector device can be adapted to measure at least one parameter such as, for example, an electric current between the working electrode and the at least one further electrode or an electric voltage between the working electrode and the at least one further electrode or a combination thereof.

An object of the present disclosure is thus to reduce or even overcome at least one of the disadvantages of the state of the art. In particular, it is an object to provide a method and a biosensor for detecting an analyte that delivers precise and reproducible results even when the sample contains certain interferents. Additionally, it is an object to provide a method and a biosensor for detecting an analyte that shows a high specificity towards the analyte and little cross reactivity with other constituents of the sample. Furthermore, it is an object to provide a method and a biosensor for detecting an analyte that has a high sensitivity in a broad concentration range of the analyte. Moreover, it is an object to provide a biosensor system for detecting an analyte in a sample that works precisely and reproducibly. A further object is to provide a simple and cost-efficient method of making a biosensor for detecting an analyte.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1A:
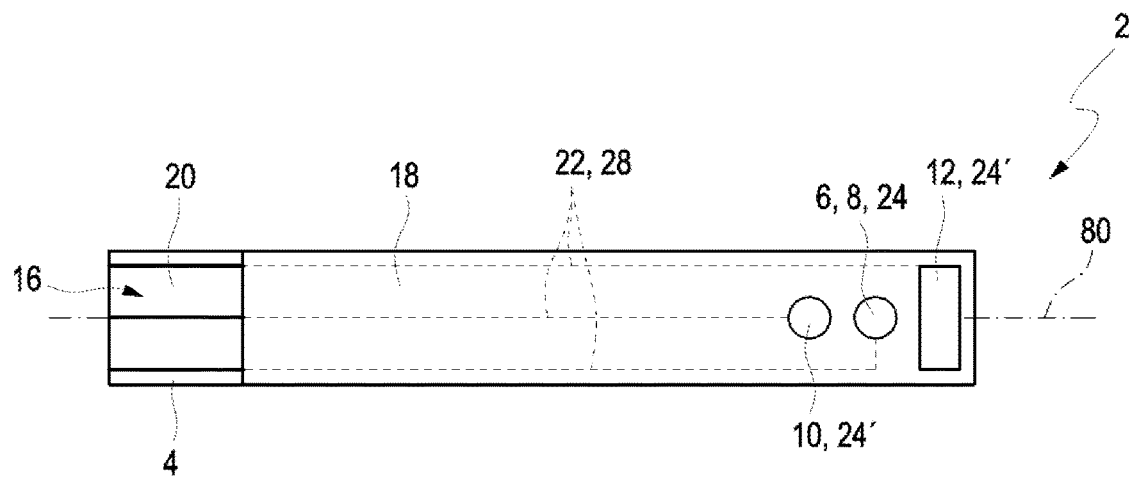
FIG. 1A shows a schematic top view of an exemplary biosensor with a working electrode, a reference electrode and a counter electrode.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, devices and systems now will be described more fully hereinafter with reference to the accompanying drawings, in which some, but not all embodiments of the inventive concept are shown. Indeed, the methods, devices and systems may be embodied in many different forms and should not be construed as limited to the embodiments set forth herein; rather, these embodiments are provided so that this disclosure will satisfy applicable legal requirements.

Likewise, many modifications and other embodiments of the methods, devices and systems described herein will come to mind to one of skill in the art to which the disclosure pertains having the benefit of the teachings presented in the foregoing descriptions and the associated drawings. Therefore, it is to be understood that the methods, devices and systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, devices and systems the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may both refer to a situation in which, besides B, no other element is present in A (i.e., a situation in which A solely and exclusively consists of B) or to a situation in which, besides B, one or more further elements are present in A, such as element C, elements C and D, or even further elements.

Overview

Biosensors, biosensor systems and their methods of manufacture and use are disclosed herein. Such biosensors and biosensor systems are based upon an inventive concept that includes using $Mn_2O_3$ particles as an electrode material. As noted above, it has been found that by using $Mn_2O_3$ particles, the reduction reaction of $H_2O_2$ can be achieved in a voltage range where a reduction of $O_2$ does not occur. The biosensors and biosensor systems therefore find use in detecting at least one analyte of interest, such as glucose, in a sample so that the effects of certain interferents are reduced on the measurement of the at least one analyte of interest.

As used herein, "analyte" means a specific compound or combination of compounds to be detected. Broad examples of an analyte of interest include, but are not limited to, amino acids, antibodies, bacteria, carbohydrates, drugs, lipids, markers, nucleic acids, proteins, peptides, toxins, viruses, and other analytes. Of interest herein are analytes such as carbohydrates, especially glucose.

As used herein, "sensor" means a device that is able to detect at least one analyte in a sample. For this purpose, the sensor may be adapted to generate a detectable signal and/or to change at least one detectable property when coming into contact with the analyte. The detectable signal generally may correlate with the concentration of the analyte in a reproducible way. As outlined above, the sensor may include at least one detection material that is adapted to perform at least one detection reaction with the analyte to be detected and/or that is adapted to change at least one detectable property in the presence of the analyte, such as an optical property and/or an electrical property. The sensor can be any sensor that detects any analyte that is able to generate $H_2O_2$. For example, the detection of the analyte can be based on an optical detection or an electrochemical detection. In particular, the detection is an electrochemical detection.

As used herein, "biosensor" generally means a sensor for detecting at least one analyte in a sample by using at least one biological detection material. Examples of a biological detection material include, but are not limited to, at least one of an enzyme, a receptor and an antibody. Additionally, the at least one detection reaction may include one or more additional components, such as one or more of a catalyst, a co-enzyme, a mediator and a dye. Thus, generally, the biosensor may include at least one detection material that may be adapted to perform at least one detection reaction with the analyte to be detected and/or that may be adapted to change at least one detectable property in the presence of the analyte, such as an electrical property and/or an optical property such as a color and/or a reflectance. When the sensor is a biosensor, the at least one detection material can be at least one enzyme, and the detection reaction can be an enzymatic reaction. Often, the product of such an enzymatic reaction is converted to create a detectable moiety. For this conversion, catalysts generally are used.

Biosensors and Biosensor Systems

Biosensors: Biosensors are provided that incorporate the inventive concept. It should be appreciated that the biosensor can have any shape as is known in the art and that would be suitable for use in the context of the present disclosure. For example, the biosensor can be a strip-shaped sensor, a sensor disk, a sensor tape, a sensor bar and a sensor needle. The sensor may include one or more test fields, where each test field has at least one detection material. Other biosensor forms include, but are not limited to, micro-arrays, lab-on-chip devices, bio-chips, bio-discs, bio-cds or other test elements. In some instances, the biosensor is disposable, whereas in other instances the biosensor is reusable.

The dimensions of the biosensor, however, can and will vary with respect to the particular analyte to be detected as well as with respect to the particular detector device to which it will be associated. General dimensions of the biosensor can include a length in a range from about 0.1 cm to about 30 cm, from about 1 cm to about 20 cm, or from about 2 cm to about 10 cm. Likewise, the biosensor can have a width in a range from about 0.1 cm to about 50 mm, from about 0.5 cm to about 20 mm, or from about 1 cm to about 10 mm. Moreover, the biosensor can have a height in a range from about 0.01 cm to about 100 mm, from about 0.05 cm to about 10 mm, or from about 0.1 cm to about 5 mm.

As used herein, "about" means within a statistically meaningful range of a value or values such as a stated concentration, height, length, molecular weight, pH, potential, time frame, temperature, voltage, volume or width. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The biosensor can be used as an electrochemical sensor for detecting the at least one analyte. As used herein, "electrochemical sensor" means a sensor having at least two sensor electrodes and adapted to detect a concentration of at least one analyte based on at least one electrical measurement, such as a measurement of a current and/or a voltage. In some instances, the at least two sensor electrodes can be at least one working electrode, the electrical potential of which may vary in accordance with the concentration of the analyte(s) to be detected and, further, at least one further electrode, such as, for example, at least one reference electrode and/or at least one counter electrode. With respect to the working electrode, it can include one or more detection materials, where the detection materials can be part of the first electrode material, may form the first electrode material, or the first electrode material may be part of the detection material.

In addition to the electrodes, the biosensor includes a substrate upon which the biosensor components can assembled and/or incorporated. The substrate can be any substrate that one of skill in the art would consider suitable for use in the context of the present disclosure. The substrate is one of the form building parts of the biosensor, so if not specified differently the specifications for the shape and dimensions also apply for the substrate. The substrate, and generally also the biosensor itself, can have a shape at least in two dimensions such as round, oval, angular or a combination thereof. Other examples of the shape of the substrate include, but are not limited to, a plate, a strip, a tape, a cube, a cuboid, a cone, a ball, a pyramid, a disc, a needle, or a combination thereof. In particular, the substrate can have a shape of a needle or a bar.

The substrate can be at least one material that can be superimposed by at least one further material. Thus, the substrate can be a solid; however, it is contemplated that the substrate can be flexible or rigid. In particular, the substrate is flexible, which means that the substrate may be deformed manually in at least one direction, such as by forces of less than about 10 N. Examples of substrates include, but are not limited to, a glass, a polymer, a ceramic, a paper, a metal oxide and a metal or a combination thereof. In some instances, the substrate is a multi-component substrate having a multi-layer setup of two or more layers, such as a laminate. In particular, the substrate can be a polymer such as, for example, a polyethylene, a polypropylene, a polystyrene, a polyester, a polyimide, or a combination thereof.

When the substrate is a polymer, it can have a molecular weight in a range from about 1,000 g/mol to about 1,000,000 g/mol, from about 5,000 g/mol to about 500,000 g/mol, or from about 10,000 g/mol to about 100,000 g/mol. Examples of polymers include, but are not limited to, polybismaleimide (PBMI), polybenzimidazole (PBI), polyoxadiazobenzimidazole (PBO), polyimidesulfone (PISO) and polymethacrylimide (PMI), or a combination thereof. In some instances, the substrate can be a polymer in a range from about 10 wt.-% to about 100 wt.-%, from about 20 wt.-% to about 95 wt.-%, or from about 30 wt.-% to about 90 wt.-%. Regardless of the number of components of the substrate, they should add up to 100 wt.-%

The substrate thus can have any form or geometry suitable for use in the biosensor. As the substrate is a main building part of the biosensor, it generally has the form or geometry as described above for the biosensor. The thickness or diameter of the substrate can be from about 0.1 mm to about 10 mm, from about 0.5 mm to about 5 mm, or from about 1 mm to about 3 mm. In the case of a cubical or cuboid extension of the substrate, the substrate can have a horizontal extension, defined as the product of the width and the length, in a range from about 1 mm$^2$ to about 100 cm$^2$, from about 10 mm$^2$ to about 50 cm$^2$, or from about 50 mm$^2$ to about 10 cm$^2$. Besides a symmetrical shape, the substrate (as well as the biosensor) can have an asymmetrical form. For example, the substrate can be L-shaped, where extensions of the longer part of the L can be in the ranges for the rectangular substrate as described above.

The substrate thus forms a sensor surface, which can be defined as the part of the surface of the substrate that will be superimposed by the conductive material and/or the electrode material. As noted above, the electrode material may form a detection material and/or may be part of a detection material. Therein, the conductive material and/or the electrode material may be in direct contact with the substrate. Alternatively, at least one intermediate layer may be interposed between the conductive material and/or the electrode material, such as an insulation layer and/or a diffusion barrier.

The sensor surface can have an area in a range from about 5% to about 90%, from about 10% to about 80%, or from about 20% to about 70% of the whole surface area of the substrate. The sensor surface of the biosensor can be provided on any side or surface of the substrate. The sensor surface can have any extension of the substrate that is accessible or contactable, at least during the production, from the outside of the biosensor or substrate. Any accessible or contactable surface of the substrate also can be named as outer surface. The extension of at least one surface of the sensor can be uniform or consistent in its shape. Likewise, the extension of a surface can be even, tilted or curved. The side or surface on which the sensor surface is provided on the substrate can be positioned on the outside of the substrate of the biosensor. The sensor surface can be the whole or at least a part of the outer surface of the substrate. The sensor surface can have any shape that the at least one surface of the substrate provides. The shape of the sensor surface can be, for example, even, tilted, angular, curved or a combination thereof.

In some instances, the substrate may have a cuboid extension, where the sensor surface may be provided on at least one of the broader sides of the substrate. The sensor surface also can be provided on one of the smaller sides of the cuboid. Furthermore, the sensor surface can be provided on more than one surface of the substrate. The sensor surface can extend on two or more surfaces of the substrate. The sensor surface can have an extension in a range from about 0.05 cm$^2$ to about 50 cm$^2$, from about 0.1 cm$^2$ to about 20 cm$^2$, or from about 0.2 cm$^2$ to about 10 cm$^2$.

The conductive material superimposes at least a part of the sensor surface. The conductive material can be any material that is suitable for use in a biosensor and can include any material that is able to conduct an electrical current. Examples of conductive material include, but are not limited to, a metal, a semimetal, a conducting polymer, a conducting inorganic material, or a combination thereof.

When the conductive material is a metal, it can be gold (Au), silver (Ag), platinum (Pt), tungsten (W), palladium (Pd), platinum (Pt), or a combination thereof. In particular, the conductive material is Au.

When the conductive material is a semimetal, it can be silicium/silicon (Si), boron (B), alpha tin (Sn), or a combination thereof.

When the conductive material is a conducting polymer, it can be a polythiophene, a polypyrrole, a polyaniline, a polyacetylene, a polyisothionaphthalene, a poly-p-phenylene, a derivative thereof, or combinations or copolymers thereof. Examples of conductive polymers include, but are not limited to, poly(p-phenylenevinylene), poly(p-phenylene sulphide), poly(3,4-ethylenedioxythiophene) or combinations thereof.

When the conductive material is a conducting inorganic material, it can be an electrically conductive ceramic material, a graphene, graphite or a combination thereof. Conductive ceramic material, also called cermet, includes a ceramic and a metallic material. The ceramic material can be one or more elements such as, for example, $O_2$, carbon (C), B, nitrogen (N), Si, or a combination thereof. Examples of ceramic material include, but are not limited to, aluminium oxide (e.g., $Al_2O_3$); zirconium oxide (e.g., $ZrO_2$); manganese oxide (e.g., MgO); zirconium toughened aluminium oxide (ZTA); aluminium nitride (AlN); aluminium titanate ($Al_2TiO_5$ or $Al_2O_3.TiO_2$); a piezoceramic such as, for example, Ba (Zr, Ti)$O_3$, Ba (Ce, Ti)$O_3$, potassium sodium niobate (PSN), PSN—LiSbO$_3$, PSN—LiTaO$_3$, or a combination thereof. The metal material of the conducting inorganic material can be a metal such as, for example, nickel (Ni), molybdenum (Mo), a Mo alloy, iridium (Ir), tantalum (Ta), a Ta alloy, cobalt (Co), a cobalt-chromium alloy, titanium (Ti), a Ti alloy, niobium (Nb), a Nb alloy, Pt, a Pt alloy, tungsten (W), a W alloy, steel, or a combination thereof. Examples of electrically conductive ceramics include, but are not limited to, tungsten silicide (WSi$_2$), tungsten carbide (WC), titanium nitride (TiN), titanium carbonitride (TiCN) and titanium carbide (TiC).

Regardless of the conductive material selected, it can be in a range from about 10 wt.-% to about 100 wt.-%, from about 20 wt.-% to about 100 wt.-%, or from about 30 wt.-% to about 95 wt.-% based on a total weight of the conductive material. In particular, the conductive material is Au in a range of from about 50 wt.-% to about 100 wt.-%, from about 70 wt.-% to about 100 wt.-%, or from about 80 wt.-% to about 100 wt.-%.

As noted above, the conductive material superimposes at least a part of the sensor surface of the substrate. The conductive material can superimpose the sensor surface in a range from about 5% to about 100%, from about 10% to about 95%, or from about 20% to about 90% by area. Likewise, the conductive material can superimpose an area of the surface of the substrate in a range from about 0.01 mm$^2$ to about 50 cm$^2$, from about 0.1 mm$^2$ to about 40 cm$^2$, or from about 0.5 mm$^2$ to about 10 cm$^2$.

By superimposing at least a part of the sensor surface by the conductive material, one or more conductive contact leads can be achieved. In some instances, more than one conductive contact lead is provided on the sensor surface. For example, three conductive contact leads can be applied to the sensor surface by superimposing, which is described in more detail below in the methods. The conductive contact leads can be separated from each other by a width in a range from about 0.1 mm to about 10 mm, from about 0.3 mm to about 5 mm, or from about 0.5 mm to about 2 mm. Each contact lead can build the basis for an electrode.

As noted above, the biosensor can include at least two electrodes, where one electrode is at least one working electrode, where the working electrode includes the conductive material and the first electrode material. As also noted above, one or more further electrodes may be include, such as one or more reference electrodes and/or one or more counter electrodes. The one or more further electrodes each may have at least one conductive material and/or at least one contact lead and, additionally or optionally, at least one further electrode material, such as at least one reference material.

Additionally, the at least one working electrode and, optionally, the at least one further electrodes, may fully or partially be covered by at least one protective layer, such as a membrane, which is permeable for the analyte to be detected and/or for at least one electrolyte of the sample, whereas the first electrode material may be retained and may be prevented from contacting the sample and/or a surrounding body tissue. Thereby, a biocompatibility of the biosensor may be provided. As an example, reference may be made to Int'l Patent Application Publication No. WO 2007/071562.

The first electrode material superimposing at least a part of the conductive material can be any material that is suitable for the purpose of the biosensors described herein. Thus, the first electrode material may be or may include at least one detection material or may form part of a detection material, as defined above. The first electrode material forms a working electrode or at least part of a working electrode.

In some instances, the first electrode material can include an arbitrary detection material and any compound that is adapted to carry out a detection reaction with the analyte of interest when a sample is applied to the working electrode.

Besides the detection material, the first electrode material can include at least one material that is able to conduct an electrical current such as a conducting material. As above, examples of conducting material include, but are not limited to, a metal, a semimetal, a conducting polymer or a combination thereof.

When the conductive material is a metal, it can be Au, Ag, Pt, W, Pd, or a combination thereof.

When the conductive material is a semimetal, it can be Si, B, Sn, or a combination thereof.

When the conductive material is a conducting polymer, it can be a polythiophene, a polypyrrole, a polyaniline, a polyacetylene, a polyisothionaphthalene, a poly-p-phenylene, a derivative thereof, combinations thereof, or copolymers thereof. Examples of conductive polymers include, but are not limited to, poly(p-phenylenevinylene), poly(p-phenylene sulphide), poly(3,4-ethylenedioxythiophene) or mixtures of at least two thereof.

When the conductive material is a conducting inorganic material, it can be an electrically conductive ceramic material, a graphene, graphite, or a combination thereof. In particular, the conductive material is graphite.

As noted above, the first electrode material can include at least one detection material, such as a material that is able to interact with the analyte of interest in the sample. The detection material can be or can include a biological component. When using at least one biological component in the sensor, specifically in the detection material, the sensor can be called a biosensor.

One characteristic of a biological component may be its ability to interact with a further component, such as the analyte of interest in the sample. In many cases, the biological component is originally derived from a living body. Examples of detection materials include, but are not limited to, an enzyme, a receptor, an antibody, a chelate, or a combination thereof.

The detection material may be capable of interacting with the analyte of interest in a way that changes at least one detectable property of the analyte or the detection material or both, such as, for example, a property that can be detected optically and/or electrically.

As part of the inventive concept, it has been recognized that the first electrode material includes $Mn_2O_3$ particles. The $Mn_2O_3$ particles catalyze at least a part of the detection reaction of the analyte or a product of the analyte in a first detection reaction with the detection material. For example, a part of the detection reaction can be an electrolysis reaction, achieved according to equation (I):

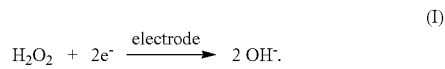
$$H_2O_2 + 2e^- \xrightarrow{\text{electrode}} 2\,OH^-. \tag{I}$$

The reaction of $H_2O_2$ shown in equation (I) is catalyzed by $Mn_2O_3$ particles. It has been found that by using $Mn_2O_3$ particles, the reduction reaction of $H_2O_2$ can be achieved in a voltage range where a reduction of $O_2$ does not occur. Thus, the resulting signal is not falsified by a reaction of $O_2$ at any of the electrodes. The detection reaction, in the form of the reduction of $H_2O_2$, can be achieved at the working electrode if a sufficient voltage is applied between the working electrode and the reference and/or counter electrode. This voltage also is called a decomposition voltage. For an electrochemical sensor, also referred to as an electrolytic sensor, the decomposition voltage of the equation (I) should be different from the decomposition voltage of the reaction of $O_2$, in form of a reduction, at the working electrode.

The decomposition voltage of a component at the working electrode can, among other things, depend on the material of the working electrode. By adding $Mn_2O_3$ particles to the first electrode material, the decomposition voltage of $H_2O_2$ can be shifted to a positive potential range. Such potential ranges are described in greater detail below in connection with the methods.

As noted above, the first electrode material superimposes at least a part of the conductive material; however, this also can mean that a part of the substrate is superimposed by the first electrode material. Superimposing at least a part of the conductive material by the first electrode material can be achieved by, for example, printing, layering, coating, impregnating or dipping or a combination thereof, which is described in greater detail below in connection with the methods.

The liquid phase or paste can be any liquid or solid matter one of skill in the art would use to carry the first electrode material. In some instances, the liquid phase includes a liquid that can dissolve at least a part of the first electrode material. For example, the liquid phase or paste can include at least one compound such as an organic compound and an inorganic compound, or combinations thereof.

Examples of organic compounds include, but are not limited to, an alcohol, an amine, an ester, an ether, a hydrocarbon, a sulfoxide, a sulfone, a sulfonate, a lactone, a lactam, a nitro compound, a nitrile, an oil, or a combination thereof. In some instances, the organic compound is an aliphatic alcohol, an aromatic alcohol, a cyclic alkene alcohol, a glycol ether, an aliphatic hydrocarbon, an aromatic hydrocarbon, a branched hydrocarbon, a benzene, a halogenated hydrocarbon, a glycol ether acetate or a combination thereof. In particular, the organic compound can be methanol, ethanol, butanol, propanol, acetone, γ-butyrolactone, N-methyl-2-pyrrolidone, acetonitrile, nitromethane, triethylamine, dimethylformamide, heptane, hexane, dimethylsulfoxide, sulfolane, ethylene carbonate, ethylene glycol monobutyl ether, dimethylcarbonate, propyleneglycol methylether acetate, propyleneglycol methylether acetate, or a combination thereof. The organic compound can be in a range from about 0.1 wt.-% to about 99 wt.-%, from about 1 wt.-% to about 95 wt.-%, from about 10 wt.-% to about 90 wt.-%, or from about 20 wt.-% to about 80 wt.-%, each based on the total weight of the liquid phase and/or paste.

Examples of inorganic compounds include, but are not limited to, water, an acid and a base, especially hydrochloric acid, nitric acid, sulfuric acid, alkaline lye, or a combination thereof. The inorganic compound can be in a range from about 0.1 wt.-% to about 99 wt.-%, from about 1 wt.-% to about 95 wt.-%, or from about 10 wt.-% to about 90 wt.-%, each based on the total weight of the liquid phase and/or paste.

The mentioned components for the liquid phase and/or paste add up to 100 wt.-%.

In addition, the liquid phase and/or paste generally can include one or more solvents and/or binders such as inorganic and/or organic solvents.

In some instances, the working electrode forms at least one working electrode pad, wherein the sample is directly or indirectly applicable to the working electrode pad. Each working electrode pad can be formed by at least one dot, line or grid, which each can form a coherent area of the first electrode material. If more than one dot, line or grid of the first electrode material is superimposed on the conductive material, the biosensor provides more than one electrode pad. All electrode pads together build the working electrode. The biosensor can include a working electrode with a number of electrode pads in a range from about 1 to about 50, from about 2 to about 30, or from about 5 to about 20.

As discussed above, it is contemplated that in some instances the biosensor can be implantable into a cavity or tissue of a living body. In such instances, the biosensor may fully or partially be covered by at least one protective layer, such as a biocompatible membrane, such as a polymethacrylate membrane, specifically a membrane covering the at least one working electrode pad.

In some instances, the conductive material of the working electrode pad is electrically connected to at least one electrically conductive contact lead.

In some instances, the first electrode material can be a material such as, for example, a graphite, an enzyme, a binder, or a combination thereof.

When the first electrode material is graphite, it can be in a range from about 10 wt.-% to about 90 wt.-%, from about 20 wt.-% to about 80 wt.-%, or from about 30 wt.-% to about 70 wt.-% based on the total weight of the first electrode material.

When the first electrode material is an enzyme, it can be in a range from about 0.1 wt.-% to about 50 wt.-%, from about 1 wt.-% to about 40 wt.-%, or from about 5 wt.-% to about 30 wt.-% based on the total weight of the first electrode material.

When the first electrode material is a binder, it can be in a range from about 0.1 wt.-% to about 20 wt.-%, from about 1 wt.-% to about 15 wt.-%, or from about 2 wt.-% to about 10 wt.-% based on the total weight of the first electrode material. The binder can be any material that brings the first electrode material in a shape to easily apply it to the conductive material such as a polymeric and/or organic binder. Examples of binders include, but are not limited to, polyvinyl alcohols, polyvinylpyrrolidones, polyvinyl chlorides, polyvinyl acetates, polyvinyl butyrates, polyacrylic acid esters, polyacrylic acid amides, polymethacrylic acid esters, polymethacrylic acid amides, polyacrylonitriles, styrene/acrylic acid esters, vinyl acetate/acrylic acid esters and ethylene/vinyl acetate copolymers, polybutadienes, polyisoprenes, polystyrenes, polyethers, polyesters, polycarbonates, polyurethanes, polyamides, polyimides, polysulfones, melamine-formaldehyde resins, epoxy resins, silicone resins or celluloses. When the binder is a polymeric organic binder, it can be produced by adding crosslinking agents, such as, for example, melamine compounds, masked isocyanates or functional silanes (e.g., 3-glycidoxypropyltrialkoxysilane, tetraethoxysilane and tetraethoxysilane hydrolysate) or by crosslinkable polymers (e.g., polyurethanes, polyacrylates or polyolefins) and subsequent crosslinking. Such crosslinking products that are suitable as polymeric binders also can be formed by, for example, reacting the added crosslinking agents with polymeric anions optionally included in the first electrode material. The mentioned components of the electrode material may add up to 100 wt.-%.

As noted above, the first electrode material includes $Mn_2O_3$ particles, which can be present in a range from about 1 wt.-% to about 90 wt.-%, from about 3 wt.-% to about 80 wt.-%, or from about 5 wt.-% to about 50 wt.-% based on the total weight of the first electrode material, particularly in a fully dried state.

The $Mn_2O_3$ particles thus can be aggregated to a further component of the first electrode material. As noted above, the first electrode material can include graphite as one component. The graphite can be provided as a liquid phase and/or paste, such as in the form of a graphite paste. A further component of the liquid phase can be an alcohol.

After drying the liquid phase and/or paste on the biosensor, the graphite and the other components of the first electrode material can form a porous mass. The $Mn_2O_3$ particles can aggregate at the surface of the porous mass. The binder therefore helps aggregate the $Mn_2O_3$ particles and other parts of the first electrode material, like the detection material, to the porous mass. By aggregating the detection material together with the $Mn_2O_3$ particles on the surface of the first electrode material, a high amount of reactive compounds on the surface of the first electrode material can be achieved. Also, the closeness of the detection material, for example an enzyme, to the $Mn_2O_3$ particles can be achieved by the porosity of the first electrode material.

In some instances, the enzyme can be an oxidase. Examples of oxidases include, but are not limited to, an alcohol oxidase, a glucose oxidase, a uricase, a monoamine oxidase, a cytochrome P450 oxidase, a NADPH oxidase, a xanthine oxidase, a L-gulonolactone oxidase, a laccase, a lysyl oxidase, or a combination thereof. In particular, the enzyme can be glucose oxidase (GOD).

In some instances, the first electrode material can be adapted so that $H_2O_2$ is generated in the detection reaction. In the biosensor, especially an electrochemical biosensor, the $H_2O_2$ can be reduced at the working electrode to generate an electrical current that can be detected. The $H_2O_2$ can be formed in the detection reaction of the analyte with the detection material in a stoichiometric relation. As used herein, "stoichiometric" means a detection reaction of one analyte molecule that delivers a natural number of $H_2O_2$ molecules or that the $H_2O_2$ molecule is built during the detection reaction from one or more analyte molecules. In some instances of the detection reaction, one, two or more $H_2O_2$ molecules are formed during the reaction of at least one analyte. For example, during the reaction of one molecule of glucose with GOD in an aqueous surrounding, one $H_2O_2$ molecule is generated according to the equation II:

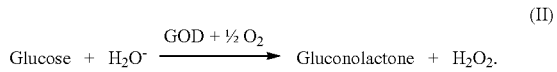

(II)

The $H_2O_2$ can be subsequently oxidized or reduced at the at least one working electrode to generate a detectable current.

To achieve a biosensor with a low resistance and therefore a low energy demand, the components of the biosensor should be selected appropriately. During the reaction according to, for example, equation (I), a current occurs or may be measured when closing an appropriate electric circuit. The current should be conducted from the working electrode to the detector device. This can be achieved by connecting the first electrode material with the conductive material. The conductive material should be able to conduct an electrical current and to be electrically connectable to a detector device. The detector device can be at least one current measurement device and/or at least one voltage measurement device, such as a potentiometer or a potentiostat. Examples of an appropriate measurement setup including a detector device are disclosed in, for example, Int'l Patent Application Publication No. WO 2007/071562. Other detector devices also can be used.

As noted above, the conducting material can be Au, Pt, Pd, Ag, or a combination thereof. The conducting material, however, also can form contacting leads, which can have a thickness in a range from about 10 μm to about 250 μm, from about 30 μm to about 180 μm, or from about 50 μm to 150 μm.

In some instances, at least a part of the biosensor is superimposed by a protective layer. Normally, the protective layer is used in a biosensor that will be introduced into the body, such as a body tissue and/or a blood vessel, of a user, such as a patient. The protective layer may function to convert the biosensor into a biocompatible device. The protective layer generally includes at least one membrane. The protective layer can be the layer that contacts parts of a body, like interstitial fluid, blood or tissue of a patient when the biosensor is implanted. The protective layer can serve as a biocompatible layer. Therefore, the protective layer can be at least partly a biocompatible material, where the biocompatible material can be in a range from about 50 wt.-% to about 100 wt.-%, from 70 wt.-% to about 100 wt.-%, or from about 90 wt.-% to about 100 wt.-% based on the total weight of the protective layer. As used herein, "biocompatible material" means a material that does not affect a living body negatively when coming into contact with the living body. To determine whether a material is biocompatible, the material can be used in accordance with ISO 10993.

In addition, the protective layer can include a polymer, a protein or a combination thereof. Examples of polymers include, but are not limited to, a polymethacrylate, a polyurethane (PU), a polyvinyl alcohol (PVA), a polyimide and a cuprophane (CUP) or a combination thereof. In particular, the protective layer can be poly(2-methacryloyloxyethyl phosphorylcholine-co-n-butyl methacrylate) (MPC), which may be solved in ethanol.

In some instances, the substrate also can include a biocompatible material, which can be the same as mentioned in the context of the protective layer. When part of the substrate, the biocompatible layer can be in a range from about 1 wt.-% to about 100 wt.-%, from about 30 wt.-% to about 100 wt.-%, or from about 50 wt.-% to about 100 wt.-%.

As briefly noted above, the biosensor can include at least one further electrode such as, for example, a reference electrode, a counter electrode, or a combined reference/counter electrode. Thus, the biosensor can have a two-electrode setup of at least one working electrode and at least one combined counter/reference electrode. Alternatively, the biosensor can have a three-electrode setup of at least one working electrode, at least one counter electrode and at least one reference electrode being separate from the counter electrode.

Like the working electrode, the at least one further electrode includes an electrode material. For example, the counter electrode can include at least one electrode material, such as a conductive electrode material such as a metal. Examples of metals for use in the counter electrode include, but are not limited to, Au, Ag, Pd, Pt, or a combination thereof.

Generally, the counter electrode includes the same components as the working electrode, with the exception of the detection material. Thus, the counter electrode can include graphite. In addition, the counter electrode can have a size where an additional reference electrode is dispensable. For example, the counter electrode can have a size for which the potential does not change more than about 10 mV during an operation of the measuring currents.

Like the working electrode and the counter electrode, the reference electrode can include at least one electrode material such as a metal, a metal sulfate, a metal halide or a combination thereof. Example of metals for use in the reference electrode include, but are not limited to, Au, Ni, Ag, mercury (Hg), copper (Cu), Pd, Pt, or a combination thereof. Example of metal halides for use in the reference electrode include, but are not limited to, AgCl, AgBr, AgI, $Hg_2Cl_2$, $CuSO_4$, or a combination thereof. In some instances, the reference electrode can include a mixture of Ag and AgCl in a range from about 1 wt.-% to about 100 wt.-%, from about 30 wt.-% to about 100 wt.-%, or from about 50 wt.-% to about 100 wt.-% based on the total weight of the reference electrode.

FIG. 1A shows schematic top view of an exemplary biosensor 2. The biosensor 2 includes a substrate 4 made from a Melinex® foil (DuPont Teijin Films, Europe). The biosensor 2 has a rectangular shape; however, the sensor 2 can have any form that is suitable to detect an analyte in a sample 26. In this example, the biosensor 2 has a length of about 2 cm, a width of about 0.5 mm and a height of about 0.15 mm in the contacting region 16. The height of the rest of the biosensor 2 might be greater than about 0.15 mm as the electrodes 6, 10, 12 and/or the isolation layer 18 may be thicker in this region of the biosensor 2. The height of the biosensor 2 in the region outside of the contacting region may be in the range from about 0.15 mm to about 2 mm.

On a sensor surface 20 of the substrate 4, three conductive contact leads 28 are positioned next to each other with a distance of about 0.05 mm each. The width of each conductive contact lead 28 is about 0.05 mm. The conductive contact leads 28 build three parallel lines made of Au. At one end of the substrate 4 (e.g., on the left hand side of FIG. 1A), a contacting region 16 is positioned. The starting points of the conductive contact leads 28 build a line perpendicular to the left border of the substrate 4. The length of each conductive contact lead 28 can vary depending on the electrode they are in contact with. In this example, the conductive contact lead 28 in the middle of the biosensor 2 is the shortest, as it is contacted to the reference electrode 10.

The conductive contact leads 28 have a length in a range from about 1.5 cm to about 1.9 cm. The longest conductive lead 28 is that contacted to the counter electrode 12. The conductive contact lead 28 contacted with the working electrode 6 provides a curve at the right end of the substrate 4 to reach that the first electrode material 24 can be positioned on the center axis 80 of the biosensor 2.

The substrate 4 can expand its width in the contacting region 16 of the biosensor 2. The contacting region 16 can have a dimension of about 0.5 cm in length, about 4.5 mm in width and about 0.15 mm in height. Thus, the width of the biosensor 2 is broadened in this part. The broadened contacting region 16 of the substrate 4 can be positioned asymmetrically, only on one side of the biosensor 2 or symmetrically on both sides of the sensor 2.

Figure 5:
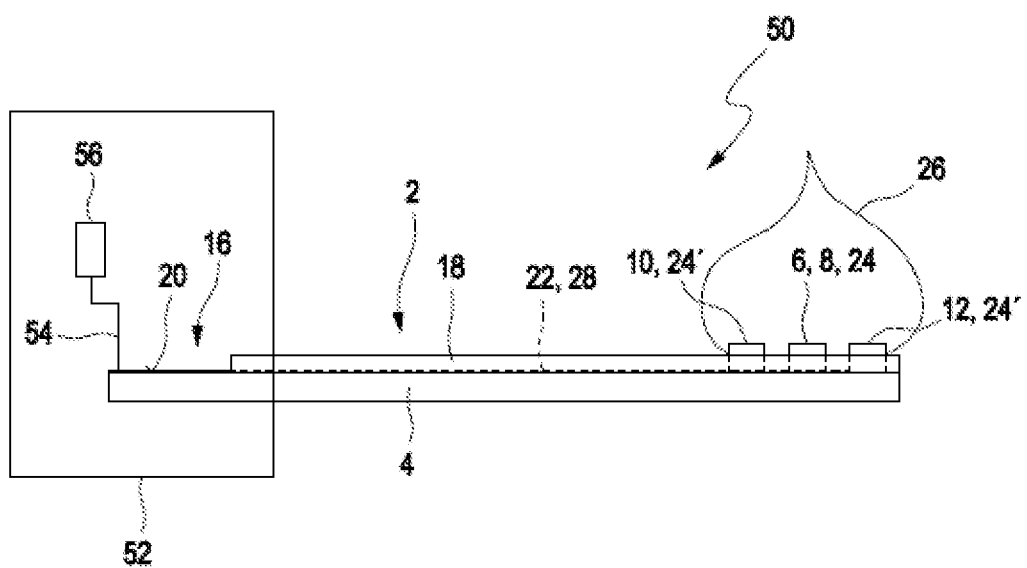
FIG. 5 shows a schematic view of an exemplary biosensor system of a biosensor with a detecting device.

In the contacting region 16, the conductive contact leads 28 might be broader than on the rest of the substrate 4. In the contacting region 16, the conductive contact leads 28 have a width of about 1 mm over a length of about 0.5 cm. The height stays the same as mentioned above. In the contacting region 16, the conductive contact leads 28 end. This is the region where a detector device 52 can be connected with the biosensor 2 as shown in FIG. 5. On the three conductive leads 28, three different electrode materials 24, 24' are positioned. The working electrode 6 includes a first electrode material 24, in the form of a graphite matrix with glucose oxidase and $Mn_2O_3$. The reference electrode 10 includes a further electrode material 24', in form of an Ag/AgCl, and the counter electrode 12 includes a further electrode material as described elsewhere herein.

An isolation layer 18 covers the working electrode 6, the reference electrode 10 and the counter electrode 12. The isolation layer 18 also can cover most of the substrate 4 and the conductive contact leads 28. The height of the isolation layer 18 is in a range from about 0.01 mm to about 0.02 mm. However, one end of each of the conductive contact leads 28 is not covered by the isolation layer 18. Alternatively, the isolation layer provides at least one hole for contacting the contact leads 28. This is the part of the biosensor 2 that can be contacted by the detector device 52. The position of the electrodes 6, 10, 12 can vary. It is not obligatory that the working electrode 6 is positioned in the middle of the three electrodes 6, 10, 12. It also is possible to position the reference electrode 10 or the counter electrode 12 in the middle of the substrate 4. If the biosensor 2 was dip coated to cover it with a protective layer, the surface opposite to the illustrated sensor surface 20 also would be covered by the protective layer (not shown here).

Figure 1B:
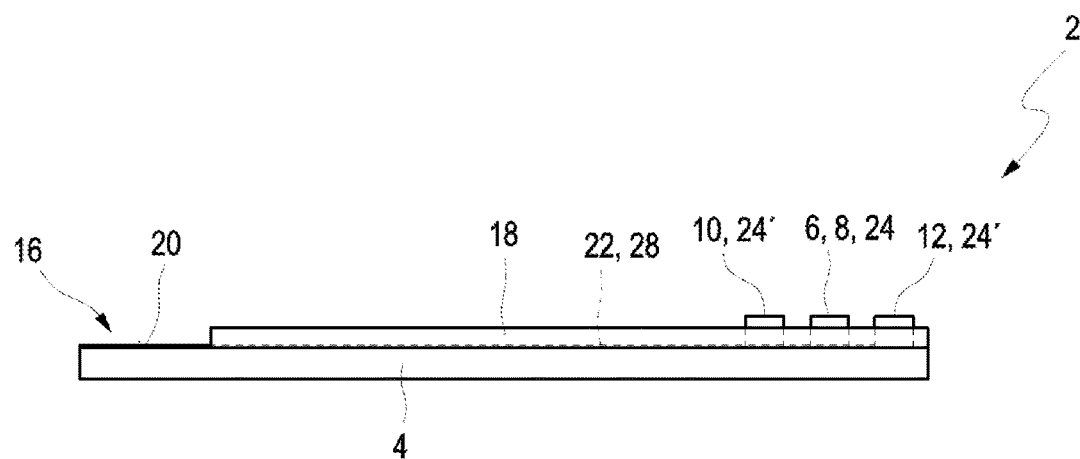
FIG. 1B shows a schematic side view of an exemplary biosensor with a working electrode, a reference electrode and a counter electrode.

FIG. 1B shows a side view of biosensor 2. Compared to the top view of FIG. 1A, the biosensor 2 in FIG. 1B is rotated about the dotted line 80 in the middle by 90°. In this side view, the sequence of the materials of the biosensor 2 is illustrated as a layered structure. At the bottom of the biosensor 2, the substrate 4 builds the first layer as base of the biosensor 2.

On the substrate 2, a layer of a conductive contact lead 28 is positioned. On the conductive contact leads 28, an isolation layer 18 is positioned, beside the contact region 16 and the part of the conductive material 22 where the first electrode material 24 is positioned to build the working electrode 6, a further electrode material 24' to build the reference electrode 10 and a further electrode material to build the counter electrode 12. Not shown in the side view is the detail that the conductive contact lead 28 is connected to the further electrode material 24' of the reference electrode 10.

There might be provided a further protective layer, such as a diffusion membrane, on the whole biosensor 2 beside the contacting region 16. Furthermore, a protective layer may cover the biosensor 2 beside the contacting region 16. The protective layer can be a biocompatible material when the biosensor is to be at least partly introduced into a living body.

Figure 2:
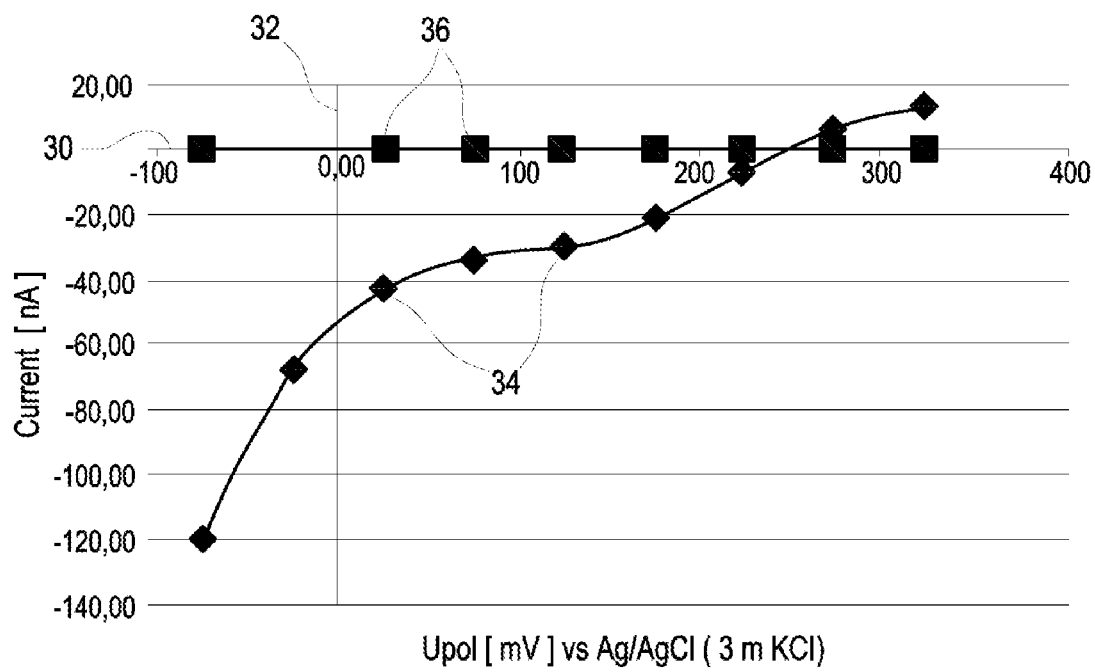
FIG. 2 shows a diagram of measurement results of two electrodes, one with and one without $Mn_2O_3$.

FIG. 2 shows a diagram of measurement values 34, 36 of two biosensors at different polarization voltages at a constant concentration of $H_2O_2$ as analyte. One of the biosensors included a working electrode 6 of PE401 (Acheson, see examples below) and is symbolized by the squares 36. The other biosensor included a working electrode 6 of $Mn_2O_3$ at 84.6 wt.-% PE401 (Acheson) and 15.4 wt.-% $Mn_2O_3$, symbolized by the diamonds 34. The counter electrodes 12 of both sensors comprised 100 wt.-% of Acheson PE401. The reference electrode 10 of both sensors comprised Electrodag 6037SS (Acheson). The two sensors with and without $Mn_2O_3$ resulting in measurement values 34 and 36 both comprised a similar composition of the counter electrodes 12.

During the measurements, the two sensors were independently positioned in a 10 mM phosphate buffer pH 7.4 with 147 mM NaCl and 50 μM $H_2O_2$ in a way that the electrodes 6, 10, 12 are dipped into the buffer solution.

The buffer solution was prepared by solving the mentioned salts in deionized water by Milli-Q Academic (Merck Millipore) for 30 minutes at a temperature of about 37° C. before adding the $H_2O_2$. The sensors were dipped into the so prepared buffer solution.

The biosensors were contacted by the contacting region to a Gamry potentiostat G300 from Gamry Instruments (USA). The power supply was regulated to supply about 325 mV (vs Ag/AgCl 3M KCl) between the working and the reference electrode at the start of the measurement. This voltage was fixed for 10 minutes. After that period the voltage was changed for eight times to a further voltage of 50 mV less than the foregoing voltage ending at −75 mV. After each change of the voltage, a measurement of the current was established for 10 minutes. The current was measured by the detector device. Results for the biosensor having $Mn_2O_3$ and for the biosensor without $Mn_2O_3$ are shown in FIG. 2.

A comparison of the measurement values 34, 36 of the two shows that the graphite electrode 10 of biosensor without $Mn_2O_3$ does not deliver a current flow when dipped into a solution of $H_2O_2$, independent of the polarization voltage applied in a range of from −75 mV to 325 mV. However, the biosensor with $Mn_2O_3$ shows a change of current starting from 325 mV to about 175 mV. From 175 mV to 25 mV, the biosensor with $Mn_2O_3$ delivers a constant current in a range of −25 to 40 nA. Not before the decrease of the voltage to 25 mV and less, the biosensor with $Mn_2O_3$ delivers stable current results. The increase of the current beyond the 25 mV to negative voltages, result in a reaction of the electrode with $O_2$ included in the solution. This is a remarkable result, as the electrodes with different metal-comprising catalysts deliver a reaction with $H_2O_2$ at lower voltages. It is surprising that a biosensor could be run with such low voltages without interference of the $O_2$ reaction.

Figure 3:
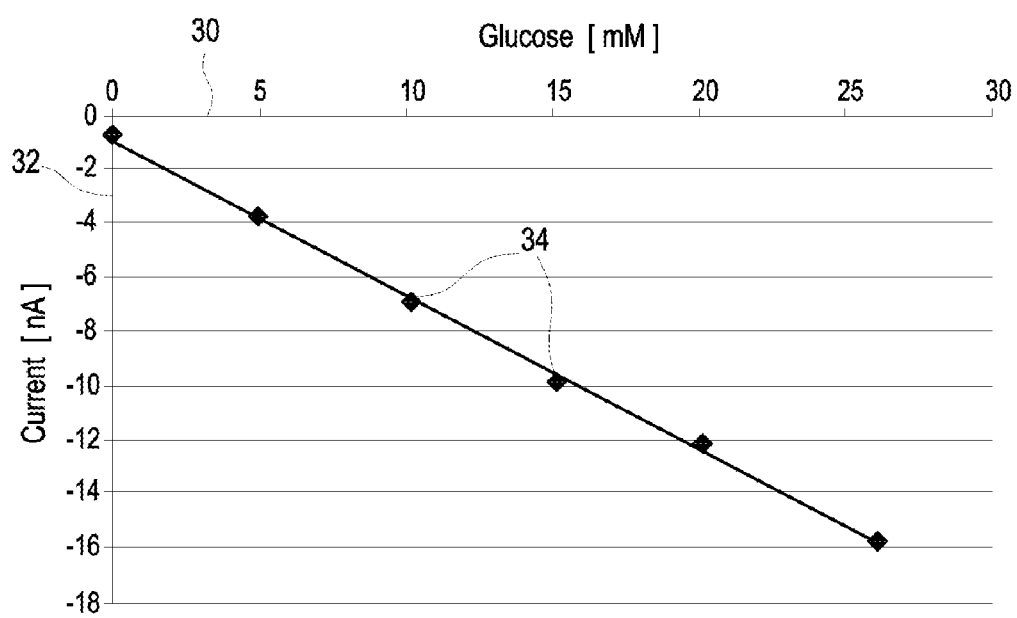
FIG. 3 shows a diagram of measurement results of an exemplary biosensor with an electrode having a $Mn_2O_3$-GOD-graphite matrix for different glucose concentrations.

FIG. 3 shows a diagram of a measurement by a biosensor 2 with a working electrode 6 having graphite, GOD and $Mn_2O_3$, a reference electrode 10 and a counter electrode 12, all prepared as described in the examples. The biosensor 2 was dipped into a buffer solution as prepared for the experiments of FIG. 2 without the addition of $H_2O_2$. The setup of the measuring system was the same as for the experiments of FIG. 2.

At a voltage of about 125 mV between the working electrode 6 and the reference electrode 10, the current was measured by the detector device. After a 25-minute equilibration, a current of 0.8 nA was measured. After this measurement, the biosensor 2 was dipped into a buffer solution as described before with 5 mM glucose. After a 25-minute equilibration the current was measured again. The current changed to 3.8 nA, as the measurement values 34 show. This was repeated for a concentration of 10, 15, 20 and 25 mM glucose in the same was as described before. The measurement values 34 show a linear increase of the current by an increase of the glucose concentration. A disturbance of $O_2$ during these measurements was not measured.

Figure 4:
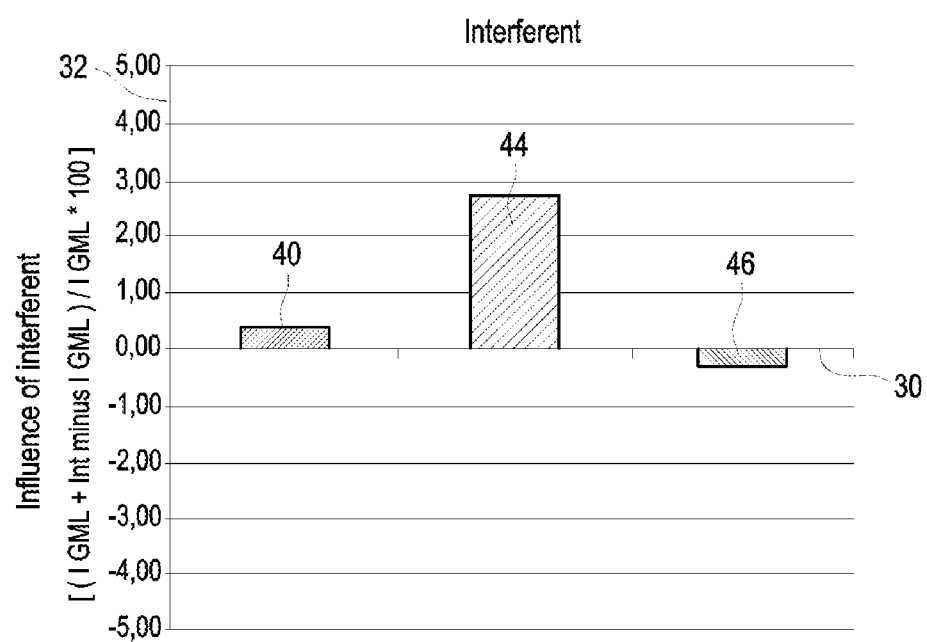
FIG. 4 shows a block diagram of results of an exemplary biosensor with a $Mn_2O_3$-GOD-graphite matrix in a 10 mM glucose solution for different interferents.

FIG. 4 shows the influence on the measurement results of a biosensor as described in FIG. 3 by adding different interferents. At a voltage of 125 mV between the working electrode 6 and the reference electrode 10, the current was measured by the detector device when one of three interferents was added to a buffer solution as described for the measurements in FIGS. 2-3, containing glucose with a concentration of 10 mM. After a 25-minute equilibration, the current was measured. A first interferent was ascorbic acid at a concentration of 2 mg/dL, which is represented by the first block 40. A second interferent was uric acid at a concentration of 8 mg/dL, which is represented by second block 44. A third interferent was acetaminophen at a concentration of 3 mg/dL, which is represented by the third block 46.

As can be seen in FIG. 4, the interference of uric acid is the greatest. Here, an increase of the signal was provoked by adding uric acid to the sample solution. The acetaminophen showed a decreasing effect on the signal of the biosensor. The ascorbic acid and acetaminophen disturbance was in the range of the normal error of measurement. As all three interfering substances show very low signal interference, the measured error of the biosensor has been diminished compared to known biosensors.

Biosensor Systems: In addition to the biosensors described above, biosensor systems incorporating the inventive concept also are provided that likewise can be used for detecting an analyte of interest in a sample. The biosensor system can include at least one biosensor as described herein and at least one detector device, where the detector device is electrically connectable to the working electrode and to at least one further electrode, where the detector device is adapted to measure at least one parameter such as an electric current between the working electrode and the further electrode and an electric voltage between the working electrode and the further electrode or a combination thereof.

The detector device can be the same as that already described in the context of the biosensor. The at least one detector device, however, should provide a voltage to the biosensor and also should measure a current that is generated by the electrodes. The at least one detector device can provide and measure a voltage. Additionally or alternatively, the at least one detector device can further provide and measure a current. Thus, the detector device can be at least one of a current measurement device and a voltage measurement device. For example, the detector device can be at least one potentiometer or potentiostat.

The detector device can be electrically connected to the biosensor by, for example, at least one contact. The contact of the detector device can contact the conductive contact lead of the biosensor to provide a voltage or a current to the electrodes, or to measure a voltage or current from the electrodes. The contact can be any contact one of skill in the art would use for providing an electrical connection. The contact can be any material that is suitable for the electrical connection of the biosensor with the detector device.

The biosensor system also can include an energy source, such as a battery. Additionally or alternatively, an external power supply can be provided. Regardless, the energy source provides energy to the detector device.

The biosensor system also can include a data memory.

The biosensor system also can include one or more user interfaces, such as one or more controls and/or one or more displays.

The biosensor system can include one or more electronic interfaces, such as wireless and/or wire-based interfaces.

In some instances, the biosensor system can be a portable biosensor system and/or a handheld device. However, other device configurations are possible.

FIG. 5 shows a biosensor system 50. A biosensor 2, with the same geometry and components as described above in FIGS. 1A-B, can be positioned with its contacting region 16 into a detector device 52. The detector device 52 provides at least one contact 54 for contacting the conductive contact leads 28 that lead to the working electrode 6, the reference electrode 10 and the counter electrode 12. In particular, each conductive contact lead 28 is contacted by one contact 54 of the detector device 52. The detector device 52 delivers and keeps a constant voltage between the working electrode 6 and the reference electrode 10. By keeping the voltage constant, the measured current between the working electrode 6 and the counter electrode 12 delivers the measurement signal that is proportional to the analyte concentration, when applying equations I and/or II. This current is measured by an electrical detector 56 that measures the current between the electrodes 6 and 12, which is part of the detector device 52.

Methods

Methods of Making Biosensors: In view of the biosensors and biosensor systems described above, methods of making the biosensors also are provided. The methods generally begin by providing a substrate having a sensor surface and then superimposing at least a part of the sensor surface by a conductive material.

The substrate can be provided by any means that allows a further step of method as described herein to be realized. Examples of means for providing a substrate include, but are not limited to, laying, uncoiling, deploying of the substrate or a combination thereof. The substrate can be provided in any manner that ensures that the sensor surface of the substrate is accessible for applying the conductive material to the substrate. The materials and properties of the substrate can be the same as already described above in connection with the biosensor. In particular, the substrate is flexible.

The substrate is then superimposed by a first conductive material on a part of the sensor surface. The conductive material can have the properties as already described above in connection with the biosensors. In some instances, the area of the sensor surface of the substrate is superimposed by a layer comprising Au in a range from about 50% to about 100%, from about 60% to about 100%, or from about 70% to about 100% of the total area of the sensor surface.

Superimposing at least a part of the first conductive material can be achieved by, for example, dispensing, doctor blading, spraying, dripping, printing, layering, coating, impregnating or dipping or a combination thereof. In some instances, the superimposing is by printing. When printing at least a part of a surface, the first electrode material can be applied as a liquid phase and/or as another form of a deformable material, such as a paste. The liquid phase and/or paste can be applied via an aid onto the sensor surface of the substrate. This can be achieved by different forms of aids. The liquid phase and/or paste can, for example, be applied via a nozzle or valve by extruding or spraying. Alternatively or additionally, the liquid phase and/or paste can be applied or printed via a roll or a drum. Examples of printing include, but are not limited to, gravure printing via a roll or ink-jet printing through an opening (e.g., a nozzle or valve), as well as screen printing through a mesh and spin coating.

When the deposition method is printing, it can be offset printing, gravure printing, inkjet printing, screen printing, spin coating, stencil printing, tampon printing, flexo printing, or a combination thereof.

When the deposition method is spin coating, it can be a chemical vapor deposition, a physical vapor deposition, a chemical and electrochemical coating, a spraying, an optical coating or a combination thereof. Examples of physical vapor deposition include, but are not limited to, a cathodic arc deposition, an electron beam physical vapor deposition (EBPVD), an ion plating, an ion beam assisted deposition (IBAD), a magnetron sputtering, a pulsed laser deposition, a sputter deposition, a vacuum deposition, a evaporation deposition like a vacuum evaporation, or a combination of at least two thereof. In particular, the superimposing is by a sputtering process of Au onto the substrate.

In some instances, the superimposing is by printing. When printing at least a part of a surface, the first electrode material can be applied as a liquid phase and/or as another form of a deformable material, such as a paste. The liquid phase and/or paste can be applied via an aid onto the sensor surface of the substrate. This can be achieved by different forms of aids. The liquid phase and/or paste can, for example, be applied via a nozzle or valve by extruding or spraying. Alternatively or additionally, the liquid phase and/or paste can be applied or printed via a roll or a drum. Examples of printing include, but are not limited to, gravure printing via a roll or ink-jet printing through an opening (e.g., a nozzle or valve), as well as screen printing through a mesh and spin coating.

During the superimposing, pressure can be applied to the liquid phase and/or paste or the substrate. Alternatively, the liquid phase and/or paste is applied using gravity alone.

The nozzle or valve can operate by a piezo element or a pneumatic valve as they are often used for ink-jet printers. These valves have a property of building portions of the applied liquid phase and/or paste that may be applied under pressure to the surface. The portions of the liquid phase and/or paste can have a volume in a range from about 0.1 nl to about 500 nl, from about 1 nl to about 100 nl, or from about 10 nl to about 50 nl.

In gravure printing, the surface to be superimposed is fed between two rolls that are in contact with each other. One roll is called the impression roll, and the other roll is called the gravure roll because the liquid phase and/or paste comes into contact with it. By guiding the substrate between the contacting rolls with the sensor surface facing towards the gravure roll, the liquid phase and/or paste can be transferred to the sensor surface of the substrate.

In screen printing, a paste typically is forced through a mesh onto the surface of the substrate. This can be achieved by gravity alone or alternatively or additional by using a squeegee or doctor knife.

In particular, superimposing can be by sputtering Au onto the sensor surface to achieve a Au layer. For superimposing the Au layer onto the substrate, the substrate can be provided as a foil of a polymer such as a polyimide.

After superimposing the Au layer onto the sensor surface, parts of the Au layer can be removed. Removal of parts of the Au layer can be achieved by any method suitable for removing metal layers from a polymeric surface. The foil can provide multiple sensor substrates, whereby the contour of each sensor substrate is embossed into the foil. To transfer the substrate from roll to roll, the foil can be provided on a first roll, where the loose end of the foil is fixed to a second roll. By fixing the foil between two rolls, at least one surface of the substrate is accessible for the next step. The accessible surface is at least a part of the sensor surface of the substrate. The accessible surface of the foil during at least one step of the method can be in a range from about 1 mm$^2$ to about 1,000 m$^2$, from about 10 mm$^2$ to about 500 m$^2$, or from about 1 cm$^2$ to about 100 m$^2$.

Regardless of the method used, the superimposing processes can be repeated several times to superimpose more than one part of the sensor surface.

A next step can include applying a first electrode material, at least on a part of the conductive material, to form a first electrode. This step can be achieved by a superimposing as described above. The first electrode can be a working electrode as described above. Thus, the first electrode material can be applied in the form a liquid phase and/or a paste. As part of the inventive concept, it has been recognized that the first electrode material includes $Mn_2O_3$ particles.

Regardless of the constituents, the liquid phase and/or paste can have a viscosity in a range from about 100 mPa·s to about 50,000 mPa·s, from about 500 mPa·s to about 10,000 mPa·s, or from about 1,000 mPa·s to about 5,000 mPa·s.

After superimposing the sensor surface by the liquid phase and/or paste having at least the first electrode material, the liquid phase and/or paste is dried to form the working electrode. Drying can be achieved by any method known to one of skill in the art and even can be supported by different drying methods. Examples of drying methods include, but are not limited to, a heating, a blowing, an irradiation or a combination of at least two thereof. In some instances, the heating can be achieved by a heating oven, by a heated surface or by a combination thereof. In some instances, the blowing can be achieved by a supply of a gas flow such as heated air. In some instances, the irradiation can be achieved by a UV lamp or an IR lamp. Regardless of the method, the drying can be achieved at a temperature in a range from about 20° C. to about 40° C. or from about 25° C. to about 35° C. Likewise, the drying can be for a time period in a range from about 1 minute to about 24 hours, from about 30 minutes to about 10 hours, or from about 1 hour to about 5 hours. By drying the liquid phase and/or paste on the substrate, the working electrode is provided.

With the application/superimposing methods, it is possible to create a pattern of the first electrode material onto the surface of the substrate. At least one dot, line or grid of the first electrode material can be formed by the superimposing method. The at least one dot or line can have a diameter or width in a range from about 0.01 mm to about 10 mm, from about 0.05 mm to about 5 mm, or from about 0.1 mm to about 1 mm. The lines of the grid can lie in the same ranges as mentioned for the dots. Moreover, the dots or the lines of the grid can have a distance or mesh size in a range from about 0.05 mm to about 10 mm, from about 0.1 mm to about 5 mm, or from about 0.5 mm to about 3 mm. As such, the at least one dot, line or grid formed of first electrode material can form the at least one working electrode or a part thereof. The dots or lines in a grid can have the same or differing extensions, especially the same or different width and length. The length of the lines of the grid can be in a range from about 0.01 mm to about 50 mm, from about 0.05 mm to about 10 mm, or from about 0.1 mm to about 5 mm. Likewise, the height of the dots or lines can be in a range from about 0.01 mm to about 10 mm, from about 0.1 mm to about 5 mm, or from about 0.5 mm to about 2 mm.

The method steps may be performed in the given order. Alternatively, other orders of the method steps are feasible. Further, one or more method steps may be performed repeatedly and/or overlapping in time. Further still, the method may comprise additional method steps.

In some instances, the method is adapted for making/manufacturing a biosensor as disclosed herein. Thus, for potential details of the method and the biosensor manufactured thereby, reference may be made to the biosensor as disclosed above or as disclosed in further detail below.

The method also can include the optional step of applying a further electrode material on at least a part of the conductive material to form a further electrode. The further electrode material can be applied in the same way as the applying of the first electrode material. In some instances, the first and/or the further electrode material can be applied by screen printing or even by screen printing in a batch process, where a foil of substrate, also called substrate foil, superimposed by the conductive material is provided. The foil can provide a number of biosensors embossed into the substrate foil in a range from about 1 to about 1,000, from about 10 to about 500, or from about 50 to about 200.

A mesh from polymer or steel can be provided on the side of the sensor surface of the substrate foil. In this instance, the electrode material of the working electrode, the reference electrode and/or the counter electrode can be applied through the mesh. The size of the mesh can be range from about 1 µm to about 300 µm, from about 5 µm to 250 µm, or from about 10 µm to about 200 µm.

Figure 6:
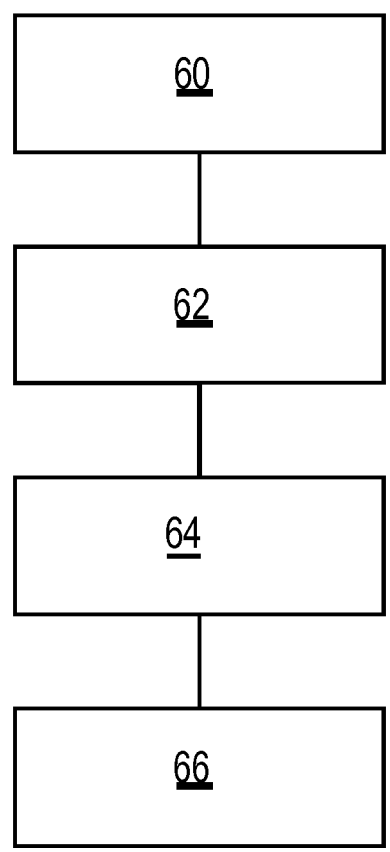
FIG. 6 shows a scheme of an exemplary method of producing a biosensor.

FIG. 6 shows an exemplary method of making a biosensor that incorporates the inventive concept. In a first step P1 60, the substrate 4 is provided, where the substrate 4 includes a sensor surface 20. Providing the substrate in the first step P1 60 is achieved by unrolling a foil of polyimide that is stored on a roll. The foil has a thickness of about 0.5 mm. One end of the foil is wound around a second roll. The distance of the rolls is in a range of from about 1 m to about 100 m. In one example, the distance is about 10 m. The foil has a width of about 1 m. The shape of the biosensor is embossed about 100 fold per meter in the foil.

A conductive material 22 in the form of Au is applied to the sensor surface 22 in the second step P2 62 by a sputtering process. The conductive contact leads 28 are formed out of the Au layer by scratching off the superfluous parts of Au.

On each sensor surface 20 of the embossed biosensors 2, the first electrode material 24 is applied to the conductive contact leads 28 in the third step P3 64 to form a working electrode 6 or a working electrode pad 8. The first electrode material 24 is applied to the conductive contact leads 28 in a way as described in herein.

In a fourth step P4 66, the reference electrode 10 and/or counter electrode 12 are applied to the conductive contact leads 28 as described herein.

Optionally a fifth step P5 can be applied (not shown) to cover at least a part of the biosensor 2 with a biocompatible membrane and/or a protective layer.

Methods of Using Biosensors: In view of the biosensors, biosensor systems and methods of making the same described above, methods of detecting an analyte of interest also are provided. The methods generally begin by providing a biosensor as described herein and contacting the biosensor to a sample.

The providing step can be achieved by any means that one of skill in the art would select for providing a biosensor in a process for detecting an analyte in a sample. Moreover, providing can be any means to provide at least a part of the biosensor to be contacted by a sample or a component that comprises the analyte such as a body, especially a tissue of a body. Examples of providing the biosensor, include, but are not limited to, to lay the biosensor on a substrate, to contact the biosensor to a sample, to insert or implant the biosensor into a living body, and to fix the biosensor to a body.

To lay the sensor on a substrate can be achieved by laying the biosensor on a substrate such as a desk, a foil or any other substrate in such a way that at least the working electrode can be contacted by the sample. Laying the sensor also can be achieved by fixing at least a part of the biosensor to a component, such as a machine, with the aim of contacting at least the working electrode with the analyte or sample.

The contacting step can be achieved by contacting at least a part of the biosensor, especially the working electrode, with the sample. The sample for in vitro analysis can be applied by any means suitable for this purpose. Examples of in vitro application include, but are not limited to, pipetting, dipping, dosing or a combination thereof. For example, the contacting can be achieved by dipping the sensor at least partly into a sample fluid. Alternatively, the sample can be applied to the biosensor, especially the working electrode, via an applying means. Examples of applying means include, but are not limited to, a pipette, a printer, a sponge or a combination thereof.

For an in-vivo biosensor, the contacting can be achieved by contacting at least the working electrode of the sensor to a living body, for example the tissue of a human body. Examples of in vivo contacting include, but are not limited to, introducing into the body and touching the body or a combination thereof. The introducing can be, for example, an implantation underneath the skin of a patient into the tissue or into the subcutaneous tissue or into a vessel. In some instances, the biosensor therefore may be an implantable sensor, which at least partially is implantable into a body tissue of a patient. The touching can be, for example, a fixation by adhesion, or a contacting of the biosensor at least with the working electrode to a region of the body where the working electrode can come into contact with the body fluid. In some instances, the sensor is introduced under the skin into the interstitial fluid. Therefore, the biosensor can be biocompatible.

In some instances, and with respect to in vivo biosensors, the biosensor can be inserted or implanted by using an insertion device. The insertion device can be arranged to enter into the body of a living body. The insertion device can provide a tip to enter into a tissue or a cavity of a living body. Alternatively, the biosensor itself can provide a tip at one end to enter the sensor into the tissue or the cavity of the living body.

In other instances, in vivo biosensors can be fixed to a living body or body part by fixing it to a tissue of a living body. The tissue can be inside or outside of the living body. Examples of tissue include, but are not limited to, skin or mucosa. The skin can be positioned anywhere on the body of the user. The mucosa can be positioned inside the nose, inside the mouth or inside the ear.

The sample therefore can be applied at least to the working electrode of the biosensor either in vitro or in vivo. The sample for in vitro analysis can have a volume in a range from about 0.001 ml to about 10 ml, from about 0.01 ml to about 5 ml, or from about 0.05 ml to about 1 ml.

Once the sample has been applied to the biosensor, the method also can include the step of applying a voltage to the working electrode by, for example, using a device that can generate a voltage between the working electrode and a further electrode such as a counter or a reference electrode or both. In general, a power source is used that supplies direct voltage. Examples of such devices includes, but are not limited to, a potentiostat, a battery, an accumulator and a power supply unit or a combination thereof. In particular, a potentionstat can be used to supply the voltage to the working electrode. To realize the application of a voltage to the working electrode, the power source can be connected to the contact leads of the biosensor, which are described in detail elsewhere. The voltage applied to the working electrode can be regulated by a voltage regulator. When contacting the working electrode, to which a voltage is applied, with the sample, $H_2O_2$ in the sample will react with the working electrode. The reaction of $H_2O_2$ at the working electrode provokes a current flow in the biosensor that can be measured by a detector device. The measured current is generally proportional to the amount of $H_2O_2$ in the sample. In at least a specific voltage range, the reaction rate of $H_2O_2$ at the working electrode is directly dependent on the diffusion rate of $H_2O_2$ in the sample. That leads to diffusion-controlled measurement of $H_2O_2$ and to a specific current measured for a specific $H_2O_2$ concentration, also called a diffusion threshold current. Thus, the measured current signal is proportional to a $H_2O_2$ concentration change in this diffusion controlled voltage range. An increase or a decrease of the voltage applied to the working electrode will not alter the reaction rate of $H_2O_2$ in this specific diffusion controlled voltage range.

As part of the inventive concept, it has been recognized that the first electrode material includes $Mn_2O_3$ particles. In view thereof, the voltage applied to the working electrode can be in a range from about 0.025 V to about 0.175 V, from about 0.050 V to about 0.150 V, or from about 0.100 V to about 0.130 V, when compared to a reference electrode of Ag/AgCl with 3 M KCl. In some instances, the voltage of the working electrode is in a range from about 50 mV to about 150 mV when compared to a reference electrode comprising Ag/AgCl with 3 m KCl. The counter electrode, the reference electrode or both can be graphite. The reference or the counter electrode can have a size in a range from about 0.1 $mm_2$ to about 10 $mm^2$, from about 0.5 $mm_2$ to about 5 $mm^2$, or from about 1 $mm^2$ to about 2 $mm^2$. The counter electrode can have a size, where an additional reference electrode is not necessary. For example, the counter electrode can have a size for which the potential does not change more than about 10 mV during an operation of the measuring currents. In some instances, the biosensor measures currents in a range from about −100 nA to about 100 nA, from about −50 nA to about 50 nA, or from about −20 nA to about 20 nA.

One positive effect of choosing a voltage in this range is that the oxidation reaction of $H_2O_2$ at the working electrode is specific. That means that, preferably, almost no other component of the sample or interferent is oxidized or reduced at the working electrode. By shifting the decomposition voltage to lower voltages, also further reactants can be reduced at the working electrode, such as $O_2$.

A current and/or a voltage can be measured and can be used as a measure of the analyte concentration. Examples of a measurement setup that may be used in the context of the biosensors disclosed herein can be found in Int'l Patent Application Publication No. WO 2007/071562. However, additionally or alternatively, other measurement setups are known in the art and may be used.

Regardless of the measurement setup, the detection can be a direct detection or an indirect detection. A direct detection can be a detection that allows the analyte to be detected without further reactions or alterations of the analyte. For example, one such direct detection may be detecting an optical property of the analyte, such as the refractive index. In contrast, an indirect detection can be a detection of a resulting compound provoked by a reaction and/or an alteration of the analyte. The alteration of the analyte in the detection reaction or alteration can be, for example, an alteration of the conformation, color, electrical charge, composition, solubility, state of aggregation or a combination thereof. For example, the alteration can be a reaction of the analyte with a compound of the sensor, whereby a further compound results that is detectable by the biosensor.

The detection reaction can provide one, two or more reaction steps. In any of the reaction steps, the analyte of interest or the detection material can provide a compound that can be detected by the biosensor. The change of property can be a change of a physical or a chemical property. Examples of physical properties include, but are not limited to, an optical property, an electrical property such as an electrical charge, a condition of aggregation, an index of refraction, a solubility, a color or a combination thereof. Examples of chemical properties include, but are not limited to, a conformation, a composition, an aggregation or a combination thereof. The result of the physical or chemical changes can be detected by a detector device. Examples of detector devices include, but are not limited to, an optical detector device and/or an electrical detector device. The optical detector device can be, for example, a CCD camera, a LED detector, a CMOS sensor or a combination thereof. The electrical detector device can be, for example, an analogue ammeter, a digital ammeter, a picoammeter, a multimeter or a combination of at least two thereof.

Thus, the methods also can include the step of determining a concentration of the analyte of interest based upon the measured $H_2O_2$-dependent current.

In the methods, the analyte of interest can be any compound or element to be detected. The analyte can be part of a sample such as, for example, a fluid or liquid. In the medical field, for example, the analyte can be a compound in a sample like a tissue or a body fluid of a patient. Examples of body fluids include, but are not limited to, blood, serum, plasma, interstitial fluid, urine, saliva, sweat or a combination thereof. The analyte of interest can be, for example, glucose, lactose, lactate, uric acid, urea, cholesterol, triglyceride and any other compound in a body fluid of a patient. The examples demonstrate proof-of-principal via electrochemical detection of glucose in blood and/or interstitial fluid.

EXAMPLES

The inventive concept will be more fully understood upon consideration of the following non-limiting examples, which are offered for purposes of illustration, not limitation.

Example 1

Methods

Preparation of Working Electrodes:

To prepare a working electrode on the substrate of the sensor a liquid phase and/or paste is superimposed on a part of the conductive material that superimposes at least a part of the sensor surface on the substrate.

The liquid phase and/or paste in the form of a paste for forming a working electrode comprises the following components:
- 66.80 wt.-% graphite PE401 (Acheson Industries Deutschland; Germany);
- 0.8 wt.-% glucose oxidase (Roche Diagnostics GmbH; Germany);
- 15.4 wt.-% $Mn_2O_3$ particles (Strem Chemicals Inc.; Germany); and
- 17 wt.-% diethylene glycol mono-n-butyl ether (DEGMBE) (Merck KGaA; Germany).

The graphite PE401 comprises:
- 36 wt.-% graphite; and
- 64 wt.-% unknown solvent.

The components are mixed twice for 5 minutes in a speed-mixer (Hauschild & Co KG; Germany) at 3000 rpm. The mixture is applied to the sensor surface to superimpose at least a part of the conductive material. The mixture is vacuum dried for 240 minutes at room temperature Preparation of Reference Electrodes:

To prepare a reference electrode on the substrate of the biosensor, a liquid phase and/or paste is superimposed on a part of the conductive material that superimposes at least a part of the sensor surface on the substrate.

The liquid phase and/or paste for forming a reference electrode comprises the following components:
- 94 wt.-% Electrodag 6037SS (Acheson Industries Deutschland; Germany); and
- 6 wt.-% DEGMBE.

The components are mixed 4 times for 15 seconds in a speed-mixer (Hauschild & Co KG, Germany) at 3000 rpm. The mixture is applied to the sensor surface to superimpose at least a part of the conductive material. The mixture is dried for 120 minutes at 80° C. at normal pressure.

Preparation of Counter Electrodes:

To prepare a counter electrode on the substrate of the sensor a liquid phase and/or paste is superimposed on a part of the conductive material that superimposes at least a part of the sensor surface on the substrate.

The liquid phase and/or paste for forming a counter electrode comprises the following components:
- 94 wt.-% graphite PE401; and
- 6 wt.-% DEGMBE.

The components are mixed for 5 minutes in a speed-mixer (Hauschild & Co KG, Germany) at 3000 rpm. The mixture is applied to the sensor surface to superimpose at least a part of the conductive material. The mixture is dried for 120 minutes at 80° C.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS 2 sensor
4 substrate
6 working electrode
8 working electrode pad
10 further or reference electrode
12 further or counter electrode
16 contacting region
18 isolation layer
20 sensor surface
22 conductive material
24 first electrode material
24' further electrode material
26 sample
28 conductive contact lead
30 x-axis
32 y-axis
34 measurement values of sensor with $Mn_2O_3$
36 measurement values of sensor without $Mn_2O_3$
40 first block/2 mg/dL ascorbic acid
44 second block/8 mg/dL uric acid
46 third block/3 mg/dL acetaminophen
50 sensor system
52 detector device
54 contact
56 electrical detector
60 step 1
62 step 2
64 step 3
66 step 4
80 dotted line/center axis of sensor 2

The invention claimed is:

1. An implantable sensor for detecting an analyte in a sample, the sensor comprising:
    a substrate, wherein the substrate comprises a sensor surface;
    a conductive material superimposing at least a part of the sensor surface of the substrate; and
    a first electrode material superimposing at least a part of the conductive material to form a working electrode, wherein the first electrode material comprises an enzyme in a range from 0.1 wt.-% to 50 wt.-% and is adapted to perform at least one detection reaction when the analyte is present in the sample, and wherein the first electrode material further comprises a catalyst configured to catalyze a reduction of hydrogen peroxide ($H_2O_2$), said catalyst comprising $Mn_2O_3$ particles, wherein the implantable sensor is covered by a biocompatible protective layer.

2. The sensor of claim 1, wherein the working electrode forms at least one working electrode pad.

3. The sensor of claim 2, wherein the at least one working electrode pad is electrically connected to at least one electrically conductive contact lead.

4. The sensor of claim 1 further comprising at least one further electrode selected from the group consisting of a reference electrode, a counter electrode, and a combined reference/counter electrode.

5. The sensor of claim 1, wherein the $Mn_2O_3$ particles are present in the first electrode material in a range from 5 wt.-% to 50 wt.-%.

6. The sensor of claim 1, wherein the first electrode material further comprises at least one material selected from the group consisting of a graphite, a binder, and a combination thereof.

7. The sensor of claim 1, wherein the enzyme is an oxidase.

8. The sensor of claim 7, wherein the oxidase is a glucose oxidase.

9. The sensor of claim 1, wherein the first electrode material is adapted such that hydrogen peroxide ($H_2O_2$) is generated during the at least one detection reaction.

10. The sensor of claim 1, wherein the conductive material comprises a component selected from the group consisting of gold, platinum, palladium, silver, and a combination thereof.

11. The sensor of claim 1, wherein the first electrode material further comprises graphite and the $Mn_2O_3$ particles are aggregated to the graphite.

12. The sensor of claim 1, wherein a usable voltage range for the sensor is from 0.025 V to 0.175 V when compared to a reference electrode comprising Ag/AgCl with 3 M KCl.

13. The sensor of claim 12, wherein the usable voltage range for the sensor is from 0.050 V to 0.150 V when compared to the reference electrode comprising Ag/AgCl with 3 M KCl.

14. The sensor of claim 1, wherein the sensor delivers electrical currents in a range from −100 nA to 100 nA.

15. A sensor system for detecting an analyte in a sample, the sensor system comprising:
at least one sensor of claim 1; and
at least one detector device, wherein the detector device is electrically connectable to the working electrode and to at least one further electrode, wherein the detector device is adapted to measure at least one parameter selected from the group consisting of an electric current between the working electrode and the at least one further electrode, an electric voltage between the working electrode and the at least one further electrode, and a combination thereof.

16. The sensor system of claim 15, where at least a part of the sensor surface is superimposed by the biocompatible protective layer.

17. A method of detecting an analyte in a sample, the method comprising the steps of:
applying a voltage to the sample in an implantable sensor comprising:
a. a conductive material, and
b. a first electrode material superimposing at least a part of the conductive material to form a working electrode, wherein the first electrode material is adapted to perform at least one detection reaction when the analyte is present in the sample and is adapted so that hydrogen peroxide ($H_2O_2$) is generated in response to the analyte during the at least one detection reaction, wherein the first electrode material comprises $Mn_2O_3$ particles and an enzyme in a range from 0.1 wt.-% to 50 wt.-%, wherein the $Mn_2O_3$ particles catalyze a reduction of hydrogen peroxide ($H_2O_2$), wherein the implantable sensor is covered by a biocompatible protective layer, and wherein the voltage is within a voltage range at which $H_2O_2$ in the sample will be reduced at the working electrode; and
detecting the analyte based upon a measured $H_2O_2$-depedent current.

18. The method of claim 17, wherein the $Mn_2O_3$ particles are present in the first electrode material in a range from 5 wt.-% to 50 wt.-%.

19. The method of claim 17, wherein the voltage range is from 50 mV to 150 mV when compared to a reference electrode comprising Ag/AgCl with 3 M KCl.

20. The method of claim 17, wherein the first electrode material further comprises at least one material selected from the group consisting of a graphite, a binder, and a combination thereof.

21. The method of claim 20, wherein the enzyme is an oxidase.

22. The method of claim 21, wherein the oxidase is a glucose oxidase and the analyte is glucose.

23. A method of making an implantable sensor for detecting an analyte in a sample, the method comprising the steps of:
providing a substrate comprising a sensor surface;
superimposing at least a part of the sensor surface by a conductive material; and
applying a first electrode material at least on a part of the conductive material to form a first electrode, wherein the first electrode material is adapted to perform at least one detection reaction when the analyte is present in the sample, wherein the first electrode material comprises an enzyme in a range from 0.1 wt.-% to 50 wt.-% and a catalyst configured to catalyze a reduction of hydrogen peroxide ($H_2O_2$), wherein said catalyst comprises $Mn_2O_3$ particles wherein the $Mn_2O_3$ particles catalyze the reduction of hydrogen peroxide, and wherein the implantable sensor is covered by a biocompatible protective layer.

24. The method of claim 23, wherein the $Mn_2O_3$ particles are present in the first electrode material in a range from 5 wt.-% to 50 wt.-%.

* * * * *